United States Patent [19]

Kanemaru et al.

[11] 4,060,564

[45] Nov. 29, 1977

[54] PROCESS FOR PREPARING ALCOHOLS

[75] Inventors: Muneaki Kanemaru, Yokohama; Tetsuo Kimura, Kamakura; Norimichi Ishii, Yokohama; Hideo Kawashima, Kamakura, all of Japan

[73] Assignee: Mitsui Toatsu Chemicals, Incorporated, Tokyo, Japan

[21] Appl. No.: 757,023

[22] Filed: Jan. 5, 1977

[30] Foreign Application Priority Data

Jan. 21, 1976 Japan .................................. 51-515043

[51] Int. Cl.$^2$ .............................................. C07C 29/08
[52] U.S. Cl. ..................................................... 260/641
[58] Field of Search .......................................... 260/641

[56] References Cited

U.S. PATENT DOCUMENTS

| 1,873,536 | 8/1932 | Brown et al. | 260/641 |
|---|---|---|---|
| 2,070,258 | 2/1937 | Coleman et al. | 260/641 |
| 2,141,275 | 12/1938 | Lewis | 260/641 |
| 2,144,750 | 1/1939 | Bent | 260/641 |
| 2,797,247 | 6/1957 | Keith | 260/641 |
| 3,459,815 | 8/1969 | Nuddings et al. | 260/641 |

*Primary Examiner*—Joseph E. Evans
*Attorney, Agent, or Firm*—Cushman, Darby & Cushman

[57] ABSTRACT

A process for preparing alcohols which comprises hydrating lower olefins in liquid phase with an aqueous 0.1 to 20.0 wt % phosphoric acid solution containing 0.001 to 1.0 wt % of an oxyacid of chromium or a salt thereof to give corresponding alcohols.

8 Claims, No Drawings

PROCESS FOR PREPARING ALCOHOLS

BACKGROUND OF THE INVENTION

1. Field of the Invention:

This invention relates to a process for preparing alcohols by catalytic hydration of olefins and more particularly, to a process for preparing alcohols by hydration of aliphatic olefins having from 2 to 12 carbon atoms in the presence of a corrosion preventive agent of a specific type.

2. Description of Prior Art:

A number of processes for preparing alcohols by direct hydration of olefins in the presence of catalysts are known. Typical of the processes are a process for hydrating olefins in the presence of heterogeneous catalysts such as of metal oxides and a process for hydrating olefins in the presence of homogeneous catalysts such as of aqueous inorganic acid solutions including sulfuric acid. It is also known that these hydration reactions are feasible either in liquid phase or in gas phase.

The liquid phase process known such as in British Pat. No. 1,281,120 and using a heteropoly-acid catalyst has the following advantages and disadvantages in comparison with the gas phase process using a phosphoric acid-on-carrier catalyst or a so-called solid phosphoric acid catalyst and known from old such as in U.S. Pat. No. 2,232,610. The liquid phase process is advantageous in that it can yield relatively high conversion rate of olefins, so that inexpensive olefins with relatively low purity are usable as starting material, but disadvantageous in that a strongly acidic catalyst is used in the form of an aqueous solution, so that a reactor or other apparatus is attacked and corroded to a considerable extent by the action of such acidic catalyst.

The corrosion tendency is likewise experienced in a liquid phase process using a phosphoric acid catalyst in the form of an aqueous solution. The phosphoric acid catalyst which is known to have relatively high hydration activity such as disclosed in Canadian Pat. No. 845,202 is a highly corrosive acid and has never been employed industrially since there is found no corrosion preventive material suitable for the above purpose. It will be noted that, in the Canadian Patent, a ceramic lined reactor is used for experiments in a laboratory scale production.

There have been studied and developed a variety of corrosion preventive agents so as to suppress the corrosion of chemical plants or apparatus. However, few of them stand use at high temperatures of above 200° C. For example, deposition film-forming corrosion preventive agents such as polyphosphoric acid salts and zinc salts show a good corrosion preventive ability only when employed at a relatively low temperature below 100° C. While, adsorption film-forming corrosion preventive agents such as some amines and surface active agents are believed that a critical temperature sufficient for giving a stable corrosion preventive effect is in the range of 150 – 160° C at a maximum when considered on an adsorption equilibrium basis (see the Material of the Eleventh Course In Corrosion and Corrosion Prevention, page 225 (1972) under the promotion of Japan Association of Materials). Further, oxidation film forming corrosion preventive agents such as chromates, molybdates and tungstates have been widely used as neutral corrosion control agents but have hardly employed against aqueous acidic solutions. These agents are considered to be reduced by the action of organic reducing materials and lose their control action (see the Hand-book of Metal Corrosion Prevention Technology, page 333 (1961) complied by the Japan Learning and Study Advancement Society). Thus, there are not yet found any corrosion preventive agents which can stand use even in a reducing atmosphere which will be experienced, for example, upon the direct hydration of olefins by a liquid phase process.

SUMMARY OF THE INVENTION

It is an object of the present invention to provide an improved process for hydrating lower olefins to prepare corresponding lower alcohols.

It is another object of the present invention to provide a process for hydrating lower olefins by a liquid phase method using a relatively inexpensive phosphoric acid hydration catalyst by which relatively high conversion rate of olefins can be attained.

It is another object of the present invention to provide a process for preparing lower alcohols from lower olefins by a liquid phase method using phosphoric acid as catalyst wherein relatively inexpensive materials of apparatus are usable while preventing the materials from being corroded.

According to the present invention, there is provided a process for preparing lower alcohols which comprises interacting a lower aliphatic olefin containing from 2 to 12 carbon atoms and water in an aqueous 0.1 to 20.0 wt % phosphoric acid solution containing an oxyacid of chromium and/or a salt of the oxyacid in an amount of 0.001 to 1.0% by weight of a total amount of the reaction solution at a temperature of 100 to 350° C under a pressure of 10 to 350 kg/cm$^2$(G).

DESCRIPTION OF THE PREFERRED EMBODIMENT

Examples of the oxyacids of chromium and the salts thereof useful in the process of the invention include, for example, chromic anhydride, chromic acid, bichromic acid, chromium (III) oxide, zinc chromate, calcium chromate, copper chromate, potassium chromate, sodium chromate, potassium bichromate, sodium bichromate, copper bichromate, and the like. These corrosion preventive agents may be used singly or in combination. Of these, the oxyacid compounds of chromium are preferable, of which chromic anhydride and chromic acid are most preferable because of excellent corrosion preventive ability. The chromates may be likewise used, of which potassium bichromate and sodium bichromate are preferable due to excellency in corrosion preventive ability. These oxyacids of chromium and/or salts thereof are formed several types of the chromium phosphate in the reaction solution.

Though the amount of the corrosion preventive agent varies depending on the kind of olefins, the reaction temperature, the reaction pressure and the concentration of phosphoric acid in the reaction solution, it is generally in the range of from 0.001 to 1.0% by weight, preferably from 0.001 to 0.1% by weight, of the reaction solution. Less amount of the corrosion preventive agent in the reaction solution less than 0.001 wt %, does not produce a practically satisfactory effect on prevention of metal materials of apparatus from corrosion. While, higher amount, i.e., exceeding 1.0 wt %, produces no problem on the corrosion preventive effect but becomes poor in economy in view of a rise in unit cost of the corrosion preventive agent.

The amount of phosphoric acid in the reaction solution will depend on the kind of olefins, the reaction temperature, and the reaction pressure but is generally in the range of from 0.1 to 20.0% by weight, preferably from 1.0 to 5.0% by weight, of the reaction solution. In an aqueous phosphoric acid solution having higher concentration, i.e., exceeding 20.0 wt % of phosphoric acid, the reaction is feasible under relatively lower temperature conditions. However, the reaction temperature can not be decreased to such a degree as to largely reduce the corrosion of the material of apparatus. Less amount of phosphoric acid, i.e., below 0.1 wt %, is unfavorable since the conversion of olefins to corresponding alcohols does not proceed satisfactorily.

The reaction temperature suitable for the process of the invention is in the range of from 100° to 350° C, with lower temperatures less than 100° C, metal materials of apparatus are substantially prevented from being corroded, requiring no corrosion preventive agent to be added. Higher temperatures than 350° C assists in accelerating corrosion of metal material. Preferably, the reaction temperature upon hydration of olefins is in the range of from 150 to 350° C but the optimum temperature varies depending on the kind of olefins within the above-defined range: a temperature ranging from 250° to 350° C is used for ethylene; from 200° to 270° C for propylene; from 150° to 200° C for butenes; and from 250° to 300° C for octenes and dodecenes.

The reaction pressure is generally in the range of from 10 to 350 kg/cm$^2$(G) but the optimum pressure varies, similarly to the reaction temperature, depending on the kind of olefins: a pressure of from 200 to 350 kg/cm$^2$(G) is used for ethylene; from 150 to 250 kg/cm$^2$(G) for propylene; from 100 to 150 kg/cm$^2$(G) for butenes; and from 10 to 60 kg/cm$^2$(G) for octenes and dodecenes.

The lower olefins which are treatable in accordance with the process of the invention are aliphatic or alicyclic unsaturated hydrocarbons containing up to 12 carbon atoms. Representative of the olefins are, for example, ethylene, propylene, n-butene, isobutene, pentene, hexene, octene and dodecene.

The starting material composition to be fed to the reaction system upon hydration of the olefins is generally more preferable, from a standpoint of chemical equilibrium, to have a greater mol ratio of water to olefin. In the practice of the invention, a mol ratio of water to lefin is in the range of from 1 to 25. In order to make the reaction to proceed more efficiently, the mol ratio is in the range of from 5 to 10 with a batch process and in the range of from 10 to 20 with a continuous process. Though the hydration reaction is feasible by a batch or continuous manner, the continuous process is desirable so as to effect the reaction efficiently. When a continuous process is employed, the reaction is conducted in a tower such as a gas absorption tower for use as a reactor in which an aqueous solution containing a catalyst and an olefin are contacted with each other either countercurrently or parallel-currently. From the reaction solution discharged from the reaction tower can be separated an unreacted olefin and a produced alcohol by a distillation or extraction. The catalyst-containing aqueous solution obtained by the separation may be added with fresh water and fed back to the reactor for reuse. While, the separated alcohol is fed to a purification step. The recovered unreacted olefin may be reused by recycle to the reaction tower.

As will be understood from the above description, one of the prominent features of the invention is that when a very small amount of a corrosion preventive agent of a specific type is added to the reaction system, materials of apparatus can be easily prevented from being corroded even under such severe reaction conditions using both a high temperature of from 100° to 350° C, and a highly corrosive acid such as an aqueous phosphoric acid.

In known processes of directly hydrating olefins in liquid phase, it has been considered necessary to use a strongly acidic aqueous solution with a low pH value so as to ensure high activity of catalyst. In addition, a reaction system containing reducing materials such as lower olefins and produced alcohols, it has been understood that oxidation film-forming corrosion preventive agents such as oxyacids of chromium and salts thereof which are employed in accordance with the process of the invention are readily reduced and lose their corrosion preventive ability. Upon judging from these past understanding, it is a marvellous fact that materials of apparatus can be prevented from being corroded in accordance with the process of the invention.

When the hydration reaction using highly corrosive acids is conducted without use of any corrosion preventive agents of the specific type employed in the present invention, a material of apparatus such as stainless steel is considerably attacked and hard to use. Additionally, even use of an expensive titanium material is insufficient to prevent corrosion, thus the hydration process using highly corrosive acids being considered impossible to be adopted for industrial purpose. In contrast, the process of the invention assures use of ordinarily employed materials of apparatus such as various kinds of stainless steels including SUS-304, SUS-316, SUS-304L and SUS-316L without causing any corrosion troubles and is thus very advantageous in economy when industrially practiced.

The present invention will be particularly illustrated by way of the following examples.

EXAMPLE 1

A test solution was prepared by dissolving 0.1 wt % of chromic anhydride to be a corrosion preventive agent in an aqueous 3.0 wt % phosphoric acid solution. Then, a 400 ml titanium autoclave equipped with an agitator was provided which had an agitating rod on which test pieces for a corrosion test were fixedly attached so as not to contact with each other by the use of a teflon sheet. 250 ml of the test solution was introduced into the autoclave and the air in the autoclave was purged and filled with a nitrogen gas. Thereafter, the content was rapidly heated while agitating, and added with propylene gas for hydration reaction when the temperature reached 250° C. During the course of the reaction the pressure was maintained at 200 kg/cm$^2$(G). The corrosion test was conducted over 126 hours under conditions of 250° C and 200 kg/cm$^2$(G). As a result, it was found that the concentration of formation of isopropyl alcohol in the reaction solution in equilibrium state was 12 wt %, and the corrosion rate of SUS-304 and SUS-316 test pieces were 0.035 mm/year and 0.014 mm/year, respectively.

When the above process was repeated using a test period of 4 hours without use of the corrosion preventive agent, it was found that the corrosion rate of SUS-304 and SUS-316 test pieces were 20.5 mm/year and 19.7 mm/year, respectively.

EXAMPLE 2

The general procedure of Example 1 was repeated using solutions of 0.1 wt % of different kinds of corrosion preventive agents shown in Table 1 in an aqueous 3.0 wt % phosphoric acid solution, different kinds of olefins and reaction conditions, all of which are shown in Table 1, with the test results of Table 1. All of the test solutions had a pH of 1.4.

Table 1

| test No. | olefin | corrosion preventive agent | temp. (°C) | pressure (kg cm² (G)) | time (hr) | tested material | corrosion rate (mm/year) |
|---|---|---|---|---|---|---|---|
| 1 | propylene | nil | 230 | 200 | 3 | SUS-304 | 152 |
| 2 | " | " | " | " | " | SUS-316 | 124 |
| 3 | " | " | " | " | " | Carpenter 20 | 124 |
| 4 | " | " | 270 | 200 | 6 | industrial titanium | 0.35 |
| 5 | " | chromic anhydride | 275 | " | 180 | SUS-304 | 0.05 |
| 6 | " | " | " | " | " | SUS-316 | 0.01 |
| 7 | " | " | " | " | " | industrial titanium | 0.00 |
| 8 | " | copper chromate | 250 | 180 | 6 | SUS-304 | 0.14 |
| 9 | " | " | " | " | " | SUS-316 | 0.21 |
| 10 | ethylene | chromic anhydride | 280 | 250 | 3 | SUS-304 | 0.02 |
| 11 | " | " | " | " | " | SUS-316 | 0.01 |
| 12 | propylene | chromic acid | 230 | 200 | 6 | SUS-304 | 0.00 |
| 13 | " | potassium bichromate | " | " | 3 | SUS-304 | 0.01 |
| 14 | " | sodium bichromate | " | " | " | SUS-316 | 0.01 |
| 15 | " | potassium chromate | 275 | " | 7 | SUS-304 | 0.63 |
| 16 | " | " | " | " | " | SUS-316 | 0.85 |
| 17 | " | sodium chromate | " | " | 24 | SUS-304 | 0.16 |
| 18 | " | " | " | " | " | SUS-316 | 0.21 |
| 19 | " | potassium chromate | " | " | 20 | SUS-304 | 0.25 |
| 20 | " | " | " | " | " | SUS-316 | 0.31 |
| 21 | " | sodium chromate and chromic anhdride | " | " | 24 | SUS-304 | 0.01 |

EXAMPLE 3

The liquid phase procedure of Example 1 was repeated using an aqueous 3.0 wt % phosphoric acid solution added with 0.1 wt % of different kinds of corrosion preventive agents, different kinds of lower olefins and reaction conditions, all of which are shown in Table 2. The test results are also shown in Table 2 below.

Table 2

| test No. | olefin | corrosion preventive agent | temp. (°C) | pressure (kg cm² (G)) | time (hr) | alcohol conc. in reaction solution (wt %) | selectivity to alcohol (%) |
|---|---|---|---|---|---|---|---|
| 1 | propylene | nil | 230 | 200 | 0.5 | 15 | 97 |
| 2 | ethylene | chromic anhydride | 230 | 250 | 3 | 6 | 99 |
| 3 | propylene | chromic anhydride | 230 | 200 | 0.5 | 15 | 97 |
| 4 | " | sodium chromate | " | " | " | 16 | 97 |
| 5 | " | copper chromate | " | " | " | 15 | 97 |
| 6 | " | calcium chromate | " | " | " | 14 | 98 |
| 7 | octene-1 | chromic anhydride | 250 | 45 | 3 | 3 | 98 |
| 8 | dodecene-1 | " | " | " | " | 2 | 99 |
| 9 | isobutylene | " | 150 | 40 | " | 16 | 97 |

COMPARATIVE EXAMPLE 250 ml of an aqueous 1.0 wt % chromic anhydride solution was introduced into a 400 ml agitated titanium autoclave, the air of which was purged and then filled with a nitrogen gas. The content was rapidly heated and propylene gas was fed into the autoclave when the temperature was reached 230° C. The pressure in the autoclave was maintained at 200 kg/cm²(G) during hydration reaction. 0.5 hours after commencement of the reaction, the autoclave was rapidly cooled and the reaction solution was withdrawn from the autoclave and subjected to a gas chromatographic analysis, revealing that the concentration of isopropyl alcohol was 1 wt %, with a small amount of acetone.

EXAMPLE 4

Two test pieces made of SUS-304 and SUS-316, respectively, were fixedly attached on an agitating rod of a 300 ml stainless steel autoclave so that they were not contacted with each other. Then, 400 ml/hr of an aqueous solution containing 0.01 wt % of chromic acid and 3.0 wt % of phosphoric acid and 90 g/hr of propylene were continuously fed into the autoclave by means of a high pressure pump. The content was rapidly heated for reaction so that the temperature was maintained at 230° C and the pressure at 200 kg/cm²(G). The reaction solution was continuously discharged from the autoclave together with unreacted propylene. 6 hours after commencement of the reaction, the test was stopped and the test pieces were removed from the autoclave. The corrosion rate were found to be 0.02 mm/year for SUS-304 and 0.01 mm/year for SUS-316. The discharged solution was subjected to a gas-chromatographic analysis, revealing that the concentration of isopropyl alcohol was 11.6 wt % and small amounts of isopropyl ether and acetone were formed.

EXAMPLE 5

Example 1 was repeated using chromic acid as the corrosion preventive agent and propylene as the olefin, and reaction conditions shown in Table 3. The test results are shown in Table 3 below. It is to be noted that the reaction pressure was 200 kg/cm²(G) and the residence time was 0.3 hrs in every test.

Table 3

| test No. | conc. of phosphoric acid (wt %) | conc. of corrosion preventive agent (wt %) | temp. (° C) | tested material | corrosion rate (mm/year) | alcohol conc. in reaction solution (wt %) | selectivity to alcohol (%) |
|---|---|---|---|---|---|---|---|
| 1 | 3.0 | 0.005 | 230 | SUS-304 | 0.34 | 10.5 | 98 |
| 2 | " | " | " | SUS-316 | 0.26 | " | " |
| 3 | " | 0.01 | " | SUS-304 | 0.05 | 11.5 | 97 |
| 4 | " | " | " | SUS-316 | 0.02 | " | " |
| 5 | " | 0.1 | " | SUS-304 | 0.01 | " | " |
| 6 | " | 1.0 | " | SUS-304 | " | " | 96 |
| 7* | 0.05 | 0.01 | " | SUS-304 | 0.01 | 0.7 | 100 |
| 8 | 0.1 | " | " | SUS-304 | 0.01 | 1.1 | " |
| 9 | 10 | 1.0 | 200 | SUS-304 | 0.31 | 11.3 | 98 |
| 10 | 20 | 1.0 | 180 | SUS-316 | 0.54 | 10.9 | 98 |
| 11* | 30 | 1.0 | 200 | SUS-304 | 3.35 | 12.1 | 97 |

Note: The experiments marked with an astrict "*" are for comparative purpose.

What is claimed is

1. A process for hydrating aliphatic olefins having from 2 to 12 carbon atoms to prepare corresponding alcohols comprising contacting said aliphatic olefins with an aqueous 0.1 to 20.0 wt % phosphoric acid solution containing a compound selected from oxyacids of chromium and salts thereof in an amount of from 0.001 to 1.0 wt % of the reaction solution at a temperature of from 100° to 350° C under a pressure of from 10 to 350 kg/cm$^2$(G) under which the reaction solution is maintained in a liquid state.

2. A process according to claim 1, wherein the content of said oxyacid of chromium and/or said salt thereof is in the range of 0.001 to 0.1 wt % and the concentration of said aqueous phosphoric acid solution is in the range of from 1.0 to 5.0 wt %.

3. A process according to claim 1, wherein said compound is an oxyacid.

4. A process according to claim 3, wherein said oxyacid is chromic acid.

5. A process according to claim 3, wherein said oxyacid is bichromic acid.

6. A process according to claim 1, wherein said compound is a salt of oxyacid.

7. A process according to claim 6, wherein said salt is sodium chromate.

8. A process according to claim 6, wherein said salt is calcium chromate.

* * * * *

UNITED STATES PATENT OFFICE
CERTIFICATE OF CORRECTION

Patent No. __4,060,564__   Dated __Nov. 29, 1977__

Inventor(s) __Muneaki KANEMARU, Tetsuo KIMURA, Norimichi ISHII and Hideo KAWASHIMA__

It is certified that error appears in the above-identified patent and that said Letters Patent are hereby corrected as shown below:

[30]   Foreign Application Priority Data

Jan. 21, 1976   Japan ................. 51-5043

Signed and Sealed this

Fourteenth Day of March 1978

[SEAL]

Attest:

RUTH C. MASON   LUTRELLE F. PARKER
Attesting Officer   Acting Commissioner of Patents and Trademarks